United States Patent [19]

Juneau et al.

[11] Patent Number: 5,710,282
[45] Date of Patent: Jan. 20, 1998

[54] PROCESS FOR PREPARING SUBSTITUTED ARYLS

[75] Inventors: Kathleen Nelson Juneau; Richard Vicari; Carl David Murphy, all of Corpus Christi, Tex.

[73] Assignee: Hoechst Celanese Corporation, Warren, N.J.

[21] Appl. No.: 516,768

[22] Filed: Aug. 18, 1995

[51] Int. Cl.⁶ ................................................. C07D 403/10
[52] U.S. Cl. ............................ 548/455; 560/39; 562/448
[58] Field of Search .......................... 560/39; 562/448; 548/497, 455

[56] References Cited

U.S. PATENT DOCUMENTS

| 5,041,516 | 8/1991 | Frechet et al. | 528/44 |
|---|---|---|---|
| 5,136,014 | 8/1992 | Figuly | 528/272 |
| 5,183,862 | 2/1993 | Figuly | 525/437 |
| 5,196,502 | 3/1993 | Turner et al. | 528/272 |
| 5,225,522 | 7/1993 | Turner et al. | 528/361 |
| 5,227,462 | 7/1993 | Turner et al. | 528/361 |
| 5,266,106 | 11/1993 | Winnik et al. | 106/22 K |
| 5,306,561 | 4/1994 | Frechet et al. | 428/402 |
| 5,362,843 | 11/1994 | Vicari et al. | 528/271 |
| 5,418,301 | 5/1995 | Hult et al. | 525/437 |
| 5,567,795 | 10/1996 | Vicari et al. | 528/206 |

*Primary Examiner*—Joseph McKane
*Attorney, Agent, or Firm*—James J. Mullen

[57] ABSTRACT

The present invention provides a novel one-step process for preparing substituted aryls which can be used as end-capping monomers for preparing highly branched macromolecule polymers that have highly controlled molecular architectures. The process comprises the steps of (a) reacting an aromatic acid with an activating carbodiimide for a sufficient period of time and under suitable conditions of temperature and pressure to form an activated aromatic intermediate, and (b) reacting said intermediate with a suitable nucleophile for a sufficient period of time and under suitable conditions of temperature and pressure to form said substituted aryl compound.

3 Claims, No Drawings

PROCESS FOR PREPARING SUBSTITUTED ARYLS

BACKGROUND OF THE INVENTION

1. Field of the Invention

The present invention relates to novel processes for preparing substituted aryls which can be used as end-capping monomers for preparing highly branched macromolecule (hyperbranched) polymers that have highly controlled molecular architectures, and which have numerous applications such as chelating agents, rheology modifiers, and drug delivery vehicles.

2. Description of Related Art

The following prior art references are disclosed in accordance with the terms of 37 CFR 1.56, 1.97, and 1.98.

*J. Chem. Soc. Perkin Trans.* 1992 (p. 2459–2469) discloses a multi-step process for preparing highly branched macromolecules with aromatic polyester inner structure and a readily modified hydrophobic/hydrophilic surface.

*Macromolecules* 1993, 26, p. 4617–4623 discloses the synthesis of all-aromatic hyperbranched polyesters with phenol and acetate end groups. The synthesis was based on the melt condensation of the $A_2B$ monomers 3,5(bis-trimethylsiloxy)benzoyl chloride and 3,5-diacetoxybenzoic acid.

U.S. Pat. No. 5,041,516 discloses a multi-step convergent process for preparing polyesters from aliphatic and aromatic monomers.

U.S. Pat. No. 5,136,014 discloses polyesters prepared from aromatic and aliphatic monomers without a core group and which are capped.

U.S. Pat. No. 5,183,862 discloses capped polyesters prepared from aliphatic and aromatic monomers without a core group.

U.S. Pat. No. 5,196,502 discloses the use of diacetoxybenzoic acids and monoacetoxydibenzoic acids to produce wholly aromatic polyesters. This patent does not teach the use of a core monomer to increase the number of surface end groups in the polymer.

U.S. Pat. No. 5,225,522 discloses multiply-branched aliphatic-aromatic polyesters and processes for preparing the same; however, there is no disclosure of a core group.

U.S. Pat. No. 5,227,462 discloses multiply-branched aliphatic-aromatic polyesters and processes for preparing the same; however, there is no disclosure of a core group.

U.S. Pat. No. 5,266,106 discloses ink compositions with dendrimer grafts.

U.S. Pat. No. 5,306,561 discloses the preparation of surface-functional polymer particles.

U.S. Pat. No. 5,362,843 discloses a process for preparing highly branched macromolecule polymers.

U.S. Pat. No. 5,418,301 discloses a process for preparing dendritic macromolecules.

Other prior art publications which are of interest in this area include the following journal articles:

Turner, R. S.; Walter, F.; Voit, B. I.; Mourey, T. H. *Macromolecules* 1994, 27, 1611.

Turner, R. S.; Voit, B. I.; Mourey, T. H. *Macromolecules* 1993, 26, 4617.

Newkome, G. R.; Lin, X.; Weis, C. D. *Tetrahedron: Asymmetry* 1991, 2, 957.

Frechet, J. M. J. *Science* 1994, 263, 1710.

Freeher, J. M. J.; Hawker, C. J.; Wooley, K. L. *Pure Appl. Chem.* A31(11) 1994, 1627.

Wooley, K. L.; Frechet, J. M. J.; Hawker, C.J. *Polymer* 1994, 35, 4489.

Hawker, C. J.; Lee, R.; Freebet, J. M. J. *J. Am. Chem. Soc.* 1991, 113, 4583.

Jansen, J. F. G. A.; de Brabander Van der Berg, E. M. M.; Meijer, E. M. *Science* 1994, 266, 1226.

Kremers, J. A.; Meijer, E. W. *J. Org. Chem.* 1994, 59, 4262.

Seebach, D.; Lapierre, J. M.; Skobridis, K.; Greiveldinger, G. *Angew. Chem. Int. Ed. Engl.* 1994, 33, 440.

Seebach, D.; Lapierre, J. M.; Greiveldinger, G.; Skobridis, K. *Helvetica Chemica Acta* 1994, 77, 1673.

Kim, Y. H. *J. Am. Chem. Soc.* 1992, 114, 4947.

All of the above cited prior art and any other references mentioned herein are incorporated herein by reference in their entirety.

SUMMARY OF THE INVENTION

The present invention provides novel processes for preparing highly branched macromolecule polymers that have highly controlled molecular architectures. These types of polymers have utility in numerous areas such as engineering resins, fiber, film, bottle resins, rheology modifiers, drug delivery systems, membranes, chelating agents, catalyst support, medical applications, analytical systems, and separation processes, in addition to being incorporated or copolymerized with other polymers such as polysulfone and polycarbonate.

The process comprises the reaction of a branching monomer ("monomer") such as a substituted phenyl compound having the formula:

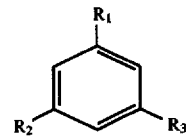

wherein $R_1$, $R_2$, and $R_3$ are defined below, with a novel second monomer ("an end-capping monomer"), hereinafter defined, such as a phenolic ester, for a sufficient period of time and at a sufficient temperature to produce the highly branched polymers in a single processing step.

DETAILED DESCRIPTION OF THE INVENTION

The present invention is directed to a novel process for preparing a highly branched polymer in a single step procedure. The present process utilizes the reaction of a certain class of substituted phenyl compounds (referred to herein as "branching monomer" or "monomer") with a new, novel class of polyfunctional molecules (herein referred to as "end-capping monomer") at a sufficient temperature and for a sufficient period of time to produce the highly branched polymer and which polymer is characterized by its high degree of branching, a branch point at each monomer unit, and a large number of chain ends or "surface" functional groups, resulting in a unique controlled macromolecular architecture. The end-capping monomer is further characterized as a monomer which contains functional groups which will only react with two of the three functional groups of the branching monomer. The desired end results are only achievable by using the herein described "new end-capping monomer" in each and every case in the condensation reaction. The use of the end-tapping monomer is thus a critical feature, without which the maximum branching could not occur.

The branching monomer (hereinafter referred to as "monomer") is a substituted phenyl compound of the formula:

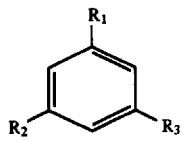
(I)

wherein $R_1$ is from the group:

COOR where R is H, alkyl ($C_1$–$C_{20}$) or aromatic;
C(O)—$OC_6H_5$;
O—$CH_2CH_2OH$;
O—C(O)—$CH_3$;
—N—$CH_2CH_2OH$; and $R_2$ is from the group:
COOR where R is H, alkyl ($C_1$–$C_{20}$) or aromatic;
OH;
$NH_2$;
O—C(O)—$CH_3$; and $R_3$ is from the group:
COOR where R is H, alkyl ($C_1$–$C_{20}$) or aromatic;
OH;
$NH_2$; and
O—C(O)—$CH_3$;

with the proviso that (a) when $R_1$ is —COOH, $R_2$ and $R_3$ must be the same but not equal to $R_1$, and $R_2$ and $R_3$ are either OH or O—C(O)—$CH_3$; (b) when $R_1$ is —C(O)—$OC_6H_5$, $R_2$ and $R_3$ are equal and are either OH or $NH_2$; and (c) when $R_1$ is O—$CH_2CH_2OH$, or N—$CH_2CH_2OH$, $R_2$ and $R_3$ are equal and $R_2$ and $R_3$ are —COOH (or —$COOR_4$ wherein $R_4$ is alkyl $C_1$–$C_4$.

Typical branching monomers falling within the above monomer formula include:

1. 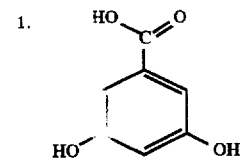 (II)

2. 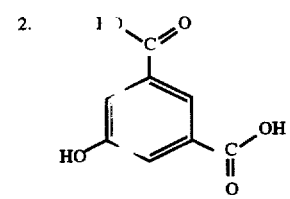 (III)

3. 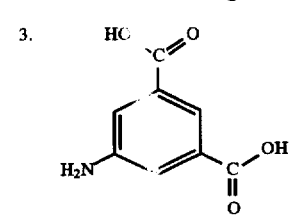 (IV)

-continued

4. 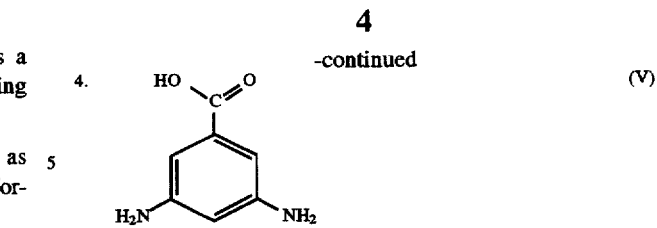 (V)

5. 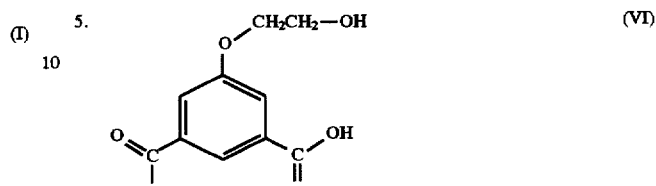 (VI)

6. 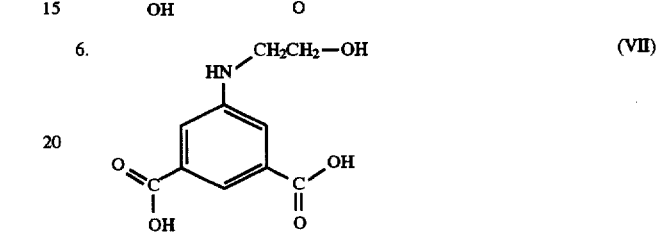 (VII)

7. 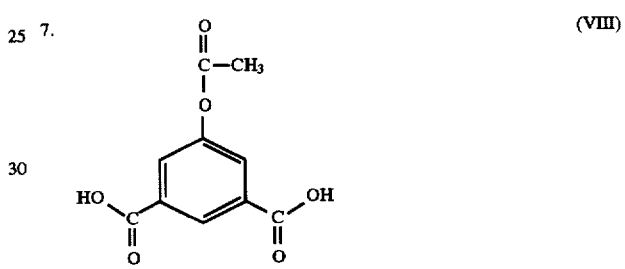 (VIII)

The end-capping monomer used in the present invention has the formula:

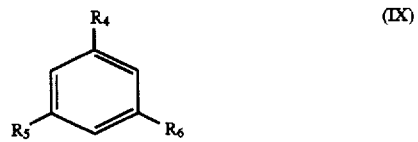
(IX)

wherein $R_4$ is selected from the group consisting of COOR wherein R is H, alkyl ($C_1$ to $C_{20}$) or aromatic; C(O)—$OC_6$—$H_5$; O—$CH_2CH_2$ OH; O—C(O)—$CH_3$; and N—$CH_2CH_2OH$. $R_5$, and $R_6$ are each independently selected from the group consisting of:

(A)  (X)

where $R_7$ is a substituted or unsubstituted aryl or alkyl group;

(B)  (XI)

where $R_8$ is a substituted or unsubstituted heterocyclic, aryl, or alkyl group and $R_9$ is H or alkyl; e.g.

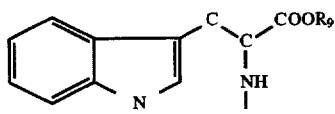

(C)    |
      $R_8-O$    (XII)

where $R_8$ is a substituted or unsubstituted heterocyclic, aryl, or alkyl group;

(D)    |
      $R_8-S$    (XIII)

where $R_8$ is a substituted or unsubstituted heterocyclic, aryl, or alkyl group;

(E)    $\underset{|}{R_4-\overset{O}{\overset{\|}{C}}}$    (XIV)

where $R_8$ is a substituted or unsubstituted heterocyclic, aryl, or alkyl group; and (F) chiral or racemic phosphine ligands.

In (E), Formula (XIV) above, this includes, without limitation, substituted or unsubstituted carboxylic acid or an optically active carboxylic acid selected from the group consisting of S-ibuprofen, S-naproxen, S-suprofen, S-flurbiprofen, S-indoprofen, S-keto-profen, S-traprofenic acid, S-fenoprofen, S-butibrifen, phenethicillin, S-2-chloropropionic acid, and ketorolac. Additional carboxylic acids are disclosed in U.S. Pat. No. 5,302,751 (Formula I), and which is incorporated herein by reference in its entirety. (E), the C(O)— is —C(O)—OH in the above acids.

The phosphine ligands (both racemic and chiral) are those which are capable of attaching to carbon in formula (IX) above. Typical phosphine ligands that can be used herein are follows: bis(triphenylphosphine) dichloro complex, bis (tricyclohexylphosphine) dichloro complex, di-allyltriphenylphosphine dichloro complex, triphenylphosphine piperidine dichloro complex, bis (triphenylphosphine (dicarbonyl complex, bis) triphenylphosphine)-diacetate complex, bis (triphenylphosphine) dinitrate complex, bis (triphenylphosphine) sulfate complex, tetrakis (triphenylphosphine) complex, and complexes in which some of the ligands are carbon monoxide such as chlorocarbonyl bis(triphenylphosphine) complex, all complexes with the end-capping monomer.

Additional phosphine ligands are disclosed in U.S. Pat. No. 4,483,802; U.S. Pat. No. 5,041,228; U.S. Pat. No. 5,057,618; German Patent DE 4,415,682, and Handbook of Enantioselective Catalysis, H. Brunner and W. Zettlmeier, Vols. I and II, VCH Verbagsgesellschaft mbH; and D-6945 1 Weinheim (Federal Republic of Germany) 1993, all of which are incorporated herein by reference in their entirety.

In addition to the definitions of $R_1-R_8$ above, $R_1-R_8$ may also include alkyl, phenyl, naphthyl, substituted phenyl, substituted naphthyl, alkenyl, alkynyl, cycloalkyl, heteroaryl, substituted heteroaryl, alkoxyalkyl, and alkylthioalkyl.

In the above definitions and throughout the present specification, alkyl means straight or branched chain alkyl having 1 to 20 carbon atoms, and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl, and eicosyl.

Cycloalkyl means cyclic alkyl having 3 to 7 carbon atoms, and includes cyclopropyl, cyclobutyl, cyclopentyl, cyclohexyl, and cycloheptyl.

Alkenyl means straight or branched chain alkenyl having 2 to 8 carbon atoms, and includes, for example, vinyl, 1-propenyl, allyl, isopropenyl, 2-butenyl, 1,2-butanedienyl, 2-pentenyl, 2-hexenyl, and octenyl.

Alkynyl means straight or branched chain alkynyl having 2 to 8 carbon atoms, and includes, for example, ethylnyl, 2-propynyl, butynyl, pentynyl, hexynyl, heptynyl, and octynyl.

Substituted phenyl and substituted naphthyl means phenyl or naphthyl substituted by at least one substituent selected from the group consisting of halogen (chlorine, bromine, fluorine, or iodine), amino, nitro, hydroxy, alkyl, alkoxy which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptryloxy, octyloxy, nonyloxy, and decyloxy, haloalkyl which means straight or branched chain alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chiorobutyl, 4-fluorobutyl, dichloromethyl, dibromomethyl, difluoromethyl, diiodomethyl, 2,2-dichloroethyl, 2,2-diboromethyl, 2,2-difluoroethyl, 3,3-dichloropropyl, 3,3-difluoropropyl, 4,4-dichlorobutyl, 4,4-difluorobutyl, trichloromethyl, 4,4-difluorobutyl, trichloromethyl, trifluoromethyl, 2,2,2-trifluoroethyl, 2,3,3-trifluoropropyl, 1,1,2,2-tetrafluoroethyl, and 2,2,3,3-tetrafluoropropyl.

Heteroaryl means 5 to 10 membered mono- or fused-heteroaromatic ring which has at least one heteroatom selected from the group consisting of nitrogen, oxygen, and sulfur, and includes, for example, 2-furyl, 3-furyl, 2-thienyl, 3-thienyol, 2-pyridyl, 3-pyridyl, 4-pyridyl, 4-pyridyl, pyrazolyl, imidazolyl, pyrimidinyl, pyridazinyl, pyrazinyl, benzimidazolyl, quinolyl, oxazolyl, thiazolyl, and indolyol.

Substituted heteroaryl means 5 to 10 membered mono- or fused-heteroaromatic ring which has at least one heteroatom selected from the group consisting of nitrogen, oxygen, and sulfur and which is substituted by at least one substituent selected from the group consisting of halogen, amino, nitro, hydroxy, alkyl, alkoxy, and haloalkyl on the above-mentioned heteroaromatic nucleus.

Haloalkyl means straight or branched chain alkyl having 1 to 10 carbon atoms which is substituted with at least one halogen as mentioned above.

Alkoxyalkyl means that the alkoxy moiety and the alkyl moiety each are straight or branched chain ones having 1 to 8 carbon atoms, and includes, for example, methoxymethyl, ethoxymethyl, propoxymethyl, isopropoxymethyl, butoxymethyl, isobutoxymethyl, tertiary butoxymethyl, pentyloxymethyl, hexyloxymethyl, heptyloxymethyl, octyloxymethyl, 2-methoxyethyl, 2-ethyloxyethyl, 2-propoxyethyl, 2-butoxyethyl, 2-hexyloxyethyl, 2-octyloxyethyl, 3-methoxypropyl, 3-ethoxypropyl, 3-propoxypropyl, 3-butoxypropyl, 3-hexyloxypropyl, 3-octyloxypropyl, 4-methoxybutyl, 4-ethoxybutyl, 4-propoxybutyl, 4-butoxybutyl, 4-hexyloxybutyl, 4-octyloxybutyl, 5-methoxypentyl, 5-ethoxypentyl, 5-propoxypentyl, 5-butoxypentyl, 5-pentyloxyphenyl, 5-hexyloxypentyl, 5-octyloxypentyl, 6-methoxyhexyl, 6-ethoxyhexyl, 6-propoxyhexyl, 6-butoxyhexyl, 6-pentyloxyhexyl, 6-hexyloxyhexyl, 6-octyloxyhexyl, 8-methoxyoctyl, 8-ethoxyoctyl, 8-butoxyoctyl, 8-hexyloxyoctyl, and 8-octyloxyoctyl.

Alkylthioalkyl means that the alkylthio moiety and the alkyl moiety each are straight or branched chain ones having 1 to 8 carbon atoms, and includes, for example, methylthiomethyl, ethylthiomethyl, propylthiomethyl, isopropylthiomethyl, butylthiomethyl, isobutylthiomethyl, tertiary butylthiomethyl, pentylthiomethyl, hexylthiomethyl, octylthiomethyl, 2-methylthioethyl, 2-ethylthioethyl, 2-butylthioethyl, 2-hexylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 4-butylthiobutyl, 6-methylthiohexyl, 6-ethylthiohexyl, 6-butylthiohexyl, 8-methylthiooctyl, 8-ethylthiooctyl, and 8-butylthiooctyl.

Phenylalkyl means that the alkyl moiety is straight or branched chain alkyl having 1 to 8 carbon atoms and includes, for example, benzyl, 2-phenylethyl, 1-phenylethyl, 3-phenylpropyl, 4-phenylbutyl, 5-phenylpentyl, 6-phenylhexyl, and 8-phenyloctyl.

Substituted phenylalkyl means above-mentioned phenalkyl which is substituted by at least one substituent selected from the group consisting of halogen, amino, nitro, hydroxy, alkyl, alkoxy, and haloalkyl on the phenyl nucleus.

Heteroarylalkyl means that the heteroaryl moiety is 5 to 10 membered mono- or fused-heteroaromatic ring having at least one heteroatom selected from the group consisting of nitrogen, oxygen, and sulfur as mentioned above and the alkyl moiety is straight or branched chain alkyl having 1 to 8 carbon atoms and includes, for example, furfuryl, 3-furylmethyl, 2-thenyl, 3-thenyl, 2-, 3-, or 4-pyridylmethyl, pyrazoylmethyl, 1-imidazolylmethyl, pyrimidinylmethyl, benzimidazolylmethyl, 2-(2-furyl)ethyl, 2-(2-thienyl)ethyl, 2-(2-pyridyl)ethyl, 2-(1-imidazolyl)ethyl, 3-(2-furyl)propyl, 3-(2-thienyl)-propyl, 3-(2-pyridyl)propyl, 3-(2-pyridyl)propyl, 4-(2-furyl)butyl, 4-(2-thienyl)butyl, and 4-(2-pyridyl)butyl.

Substituted heteroarylalkyl means that the substituted heteroaryl moiety is 5 to 10 membered mono- or fused-heteroaromatic ring which is substituted by at least one substituent selected from the group consisting of halogen, amino, nitro, hydroxy, alkyl, alkoxy, and haloalkyl on the heteroaryl nucleus and which has at least one heteroatom selected from the group consisting of nitrogen, oxygen, and sulfur as mentioned above, and that the alkyl moiety is straight or branched chain alkyl having 1 to 8 carbon atom.

Cycloalkylalkyl means that the cycloalkyl moiety is cyclic alkyl having 3 to 7 carbon atoms and the alkyl moiety is straight or branched chain alkyl having 1 to 8 carbon atoms, and includes, for example, cyclopropylmethyl, cyclobutylmethyl, cyclopentylmethyl, cyclohexylmethyl, cycloheptylmethyl, 2-cyclopropylethyl, 2-cyclopentylethyl, 2-cyclohexylethyl, 3-cyclopropylpropyl, 3-cyclopentylpropyl, 3-cyclohexylpropyl, 4-cyclopropylbutyl, 4-cyclopentylbutyl, 4-cyclohexylbutyl, 6-cyclopropylhexyl, and 6-cyclohexylhexyl.

The end-capping monomer (i.e. the substituted aryl group) is prepared, in general, by reacting an aromatic acid with, for example, an activating carbodiimide (see *Tetrahedron: Asymmetry* 1991 above for examples of such activating carbodiimide) to form an activated intermediate which is then reacted with a nucleophile to form said substituted aryl group. These reactions are carried out at temperatures in the range of from about −20° C. to about 120° C., preferably from about 0° C. to about 35° C. The pressure is not critical and thus can be subatmospheric, atmospheric, or super atmospheric. A typical process of preparing an end-capping monomer is shown in Scheme 1.

SCHEME 1

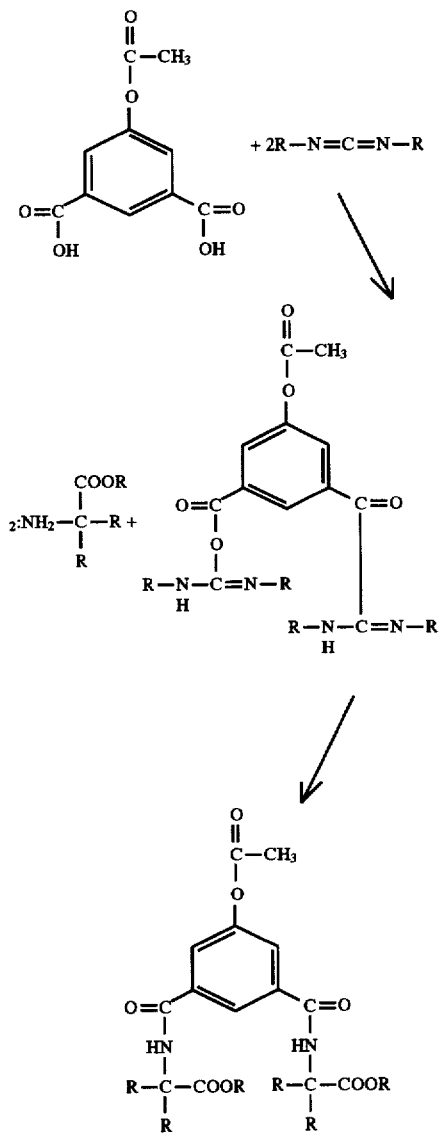

Furthermore, and as used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

The reaction of the branching monomer with the end-capping monomer may be carried out in the presence of an inert diluent which has a boiling point of from about 200° C. to about 350° C., preferably from about 220° C. to about 300° C.

Suitable diluents which assist in achieving the objects of the present invention include, without limitation, diphenyl ether, halogenated diphenyl ether, diphenyl sulfone, benzophenone, polyphenyl ethers such as tri and tetraphenyl ether, terphenyl, tetraphenyl, halogenated biphenyl, and the like.

These and other suitable diluents are disclosed in U.S. Pat. No. 3,948,856 and Ing. Eng. Chem. Prod. Res. Dev., Vol. 20, No. 2, 1981; both of these are incorporated herein by reference in their entirety.

Other suitable diluents include a poly (fluorinated alkylene oxide) having repeating units as follows:

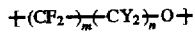

wherein m is an integer from 1 to 10, n is an integer from 0 to 5, Y is the same or different and represents hydrogen or halogen including F, Cl or Br. The poly(fluorinated alkylene oxide) can be either a straight or branched chain structure.

It is preferred that the polyether diluent be perfluorinated. Examples of the useful aliphatic polyethers used in the present invention include poly(tetrafluoroethylene oxide), poly(hexafluoropropylene oxide), poly(fluorinated butylene oxide), copolymers formed from different fluorinated alkylene oxides, etc. The polyethers used in the present invention are a non-solvent for the highly branched polymer which is formed and further, will separate from the acetic acid by-product to form a separate layer therefrom. Thus, removal of the diluent can be achieved by decantation of the diluent layer which then can be recycled to the polymerization stage. The polyether diluents used in this invention are non-flammable and non-toxic.

The poly(fluorinated alkylene oxides) used in the present invention are of relatively low molecular weight. Thus, molecular weights ($M_n$) of about 600 to 20,000 are typical with molecular weights of about 600 to 5,000 being more typical and preferred.

The diluent used, if desired, in the present invention should be present in amounts of from about 10 to about 60 wt. % based on the weight of the total charge. Preferred amounts of the diluent range from about 10 to about 40 wt. % and most preferably from about 10 to 30 wt. % based on total charge.

The amount of the diluent can vary during the polymerization reaction. For example, it may be advantageous to increase progressively the amount of the diluent to maintain the reaction medium at about constant viscosity.

It is also within the scope of the present invention to employ a reaction catalyst or a mixture of reaction catalysts. The overall objective is to use catalysts to accelerate the rate of polymerization of the reaction mixture. These catalysts are sometimes called esterification catalysts.

All the conventional catalysts being capable of accelerating an ester exchange reaction are usable. Suitable examples of catalysts are salts or compounds of elements selected from Groups 1A, 2A, 2B, 3A, 4A, and 5A of the periodic table of elements. Examples include metal oxides (e.g., magnesium oxide, lead oxide, zinc oxide, antimony trioxide); alkoxides which are prepared by the reaction of an alcohol or glycol and an alkali metal, alkaline earth metal, aluminum or titanium; sodium acetate and sodium benzoate; metal hydrides and metal borohydrides (e.g., lithium hydride, potassium borohydride ($K_2B_2H_6$). One preferred catalyst is an alkali metal salt and most preferred are lithium and potassium salts including the acetates, carbonates, benzoates, formates, bicarbonates, hydroxides, phosphates, and monohydrogen phosphates of lithium or potassium. The lithium salts are especially preferred including lithium acetate, carbonate, and hydroxide. The catalyst is added in amounts between about 5 to 100 ppm based on end-capping monomer, preferably about 20 to 50 ppm, and most preferably about 25 ppm.

Additional catalysts may also be used, in combination with the above described catalysts. Examples include the imidazole catalysts disclosed in U.S. Pat. No. 4,612,360 incorporated herein by reference in its entirety. Specific examples include 1-methyl-imidazole, 1-ethylimidazole, 2-ethyl-4-methylimidazole, and benzimidazole.

A cobalt salt may be added to the reaction medium along with the catalyst, to act as co-catalyst and as well to yield a highly branched polymer of suitable color, in particular, improved Hunter b color in which the yellowness of the highly branched polymer is substantially reduced. Cobalt has a catalytic effect in the overall process and can reduce the yellow color in the "as-prepared" highly branched polymer formed by the present process. Any cobalt salt may be used as the co-catalyst to improve highly branched polymer color, including but not limited to, cobalt acetate, cobalt benzoate, cobalt carbonate, cobalt phenate, and the cobalt salt of aliphatic or isoaliphatic carboxylic acids which contain 3 to 20 carbon atoms, such as cobalt 2-ethylhexanoate. The cobalt salt can be added directly to the monomeric components or, more preferably, to insure solubility and uniform dispersion of the cobalt salt, the cobalt salt can be dissolved in the said diluent prior to addition. In general, the cobalt salt can be added in sufficient amounts to yield at least about 20 ppm, preferably at least 25 ppm of cobalt in the final highly branched polymer. Below these levels, some color improvement has been found although water white color is not achieved. More preferably, the amount of cobalt should range from about 30 ppm to 60 ppm based on the final polymer. The preferred highly branched polymer color has a value of less than 2.0 on the Hunter b scale.

The process of this invention is carried out at a polymerization temperature of at least 25° C., preferably from about 25° C. to about 275° C., and more preferably, from about 150° C. to about 250° C. The present process, where one so desires, may be conducted in an inert atmosphere (such as argon or nitrogen). It is desirable to maintain the reaction temperature as low as possible to prevent the coloration of polymer while as high a reaction temperature as possible is preferred in terms of the rate of reaction. The process is initially carried out at atmospheric pressure or super atmospheric pressure and the pressure can be reduced as polymerization proceeds. Near the end of polymerization, pressure as low as 0.1 mm Hg absolute may be used.

The polymerization reaction is conducted for a period of time sufficient to produce a highly branched polymer and which time is generally in the range of from about ½ hour to about 8 hours or longer, depending on the particular highly branched polymer being prepared.

The polymerization reaction of this invention may be carried out batchwise or continuously by using appropriate staging and by using suitable apparatus. Moreover, the reactants may be added to the polymerization zone in any way or order desired.

The ester derivatives of the end-capping monomer and the branching monomer may be formed in situ by adding the monomer together with the acid anhydride, said diluent, and the reaction catalyst to the reactor and the reaction carried out in a single reaction zone under combined esterification and polymerization conditions as described above. Additionally, the ester derivative of the end-capping monomer and the branching monomer may be first prepared and then a diluent and reaction catalyst added directly to the same reaction vessel with the polymerization being carried out under the conditions described above.

The highly branched polymer having the desired characteristics is recovered in its final form by methods well known to those in the art, such as by direct devolatilization in an extruder under conditions sufficient to remove the by-product compounds, coagulation, spray drying, and the like.

The highly branched polymers may be prepared in the presence of materials such as molecular weight regulators, antioxidants, and the like. The highly branched polymers obtained by the process of this invention may be used together with the well-known additives such as plasticizers, pigments, lubricating agents, mold release agents, stabilizers, inorganic fillers, and the like. These highly branched polymers may also be blended with other polymers.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

EXAMPLE 1

Preparation of 5-Acetoxyisophthalic Acid from 5-Hydroxyisophthalic Acid (Branching Monomer)

5-Hydroxyisophthalic acid (360.56 g, 1.98 moles) was charged to a 2000 mL round bottom 3-neck flask with a Friedrich condenser and thermocouple under a blanket of nitrogen. Acetic anhydride (801.25 g, 7.96 moles) was added slowly. The white suspension was stirred and refluxed (~136° C.) for 4 hours. After cooling the white solid was filtered off and washed with toluene. Yield of 5-acetoxyisophthalic acid (331.95 g, 76%, HPLC 97% purity). DSC m.p. 208° C. 1H NMR (400 MHz, $d_6$-DMSO) δ 13.33, 8.34, 7.88, 2.31. 13C NMR (100 MHz, $d_6$ DMSO) δ 169.07, 165.76, 150.63, 132.6, 127.11,126.57, 20.79.

EXAMPLE 2

Preparation of 3,5-Diacetoxybenzoic Acid from 3,5-Dihydroxybenzoic Acid (Branching Monomer)

3,5-Dihydroxybenzoic acid (444.42 g, 2.89 moles) was charged to a 2000 mL round bottom 3-neck flask with a Friedrich condenser and thermocouple under a blanket of nitrogen. Acetic arkhydride (1515 g, 14.85 moles) was added slowly. The suspension was stirred and refluxed (~135° C.) for 3 hours. After cooling, the cream solid was filtered off and washed with toluene. The acetic anhydride was removed under reduced pressure 2 more times to yield additional cream solids. Yield of 3,5-iacetoxybenzoic acid (347.02 g, 50%, HPLC 97.5% purity). DSC m.p. 155° C. 1H NMR (400 MHz, $d_6$-DMSO) δ 13.31, 7.59, 7.28, 2.29. 13C NMR (100 MHz, $d_6$-DMSO) δ 169.20, 166.01, 151.15, 133.12, 120.53, 120.32, 20.70 MS (DI') m/e 238 (M+).

EXAMPLE 3

Preparation of 2-{3-Acetoxy-5-[2-(1H-Indol-2-yl)-1-Methoxycarbonyl-Ethylcarbamoyl]-Benzoylamino}-3-(1H-Indol-2-yl)-Propionic Acid Methyl Ester (End Capping Monomer)

Acetoxyisophthalic acid (13.44 g, 0.06 moles) dissolved in tetrahydrofuran (ca. 250 mL) and 1,3-dicyclohexylcarbodiimide (27.26 g, 0.132 moles) dissolved in acetonitrile (ca. 270 mL) were added to a suspension of L-tryptophan methyl ester hydrochloride (33.69 g, 0.132 moles) in acetonitrile (ca. 1L) under nitrogen. Triethylamine (13.72 g, 0.132 moles) was added dropwise to the suspension. After stirring at ambient temperature for 2 days, the yellow solution with white precipitate was filtered and the solvent removed under reduced pressure. The residue was taken up in methylene chloride (ca. 400 mL) and filtered. The organic layer was extracted with water (1×300 mL), 5% acetic acid (3×300 mL), water (3×300 mL), dried (MgSO$_4$), filtered, and the solvent removed under reduced pressure to yield a cream foam (40.72 g, yield >100%, purity by HPLC 64%). Chromatography of the solid on silica gel with THF/methylene chloride (1:5) gave a material yield of 68%, HPLC average purity 84%. $[\alpha]_D^{20}$=−57.105° (c=1.14, methanol) HPLC purity 96%. DSC ~115° C. (broad). 1H NMR (400 MHz, $d_6$-DMSO) δ 10.84 (d, 2H, HN(trp)), 9.06 (d, 2H, NH), 8.28 (s, 1H, Ar-H), 7.79 (s, 2H, Ar-H), 7.59 (d, 2H, Ar-H(trp)), 7.35 (d, 2H, Ar-H(trp)), 4.79 (m, 2H, C*), 3.66 (s, 6H, COOCH$_3$, 3.31 (m, 4H, CH$_2$), 2.35 (s, 3H, COCH$_3$). 13C NMR (100 MHz, $d_6$-DMSO) δ 172.27 (COOCH$_3$), 169.09 (COCH$_3$), 164.93 (CON), 150.17 (Ar-C), 136.12 (indolyl-C), 135.28 (Ar-C), 127.05 (indolyl-C), 124.27, 123.81, (Ar-C), 123.56, 120.98, 118.42, 117.98, 111.45, 109.86 (indolyl-C), 53.98 (C*H-NH), 51.91 (COOCH$_3$), 26.61 (CH$_2$), 20.69 (COCH$_3$), 26.61 (CH$_2$), 20.69 (COCH$_3$)- FTIR (KBr) v 3393 (b, NH indole, NH amide), 1766 (sh, C=O), 1731 (s, C=O), 1647 (s, CO amide) cm$^{-1}$. MS(APCI(H$_2$O)+Q1) m/e 625.4 (M+1).

This end-capping monomer has the following structure:

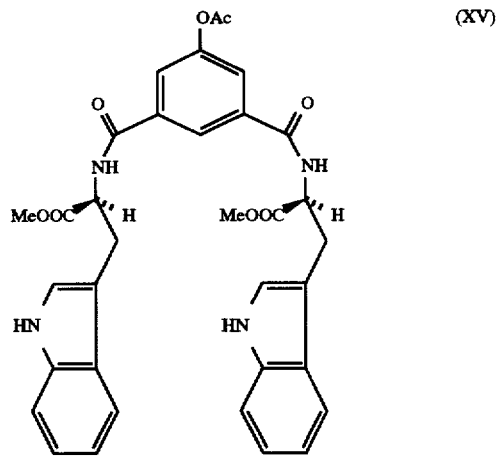

(XV)

EXAMPLE 4

Preparation of [3-Acetoxy-5-(Methoxycarbonyl-Phenyl-Methylcarbamoyl)-Benzoylaminol-Phenyl-Acetic Acid Methyl Ester (End Capping Monomer)

Acetoxyisophthalic acid (5.38 g, 0.024 moles) dissolved in tetrahydrofuran (ca. 75 mL) and 1,3-dicyclohexylcarbodiimide (10.48 g, 0.05 moles) dissolved in tetrahydrofuran (ca. 50 mL) were added to a suspension of (R)-(-)-2-phenylglycine methyl ester hydrochloride (10.45 g, 0.05 moles) in acetonitrile (45 mL) under nitrogen. Triethylamine (5.33 g, 0.05 mL) was added dropwise over 5 minutes to the suspension. After stirring at ambient temperature for 5 days, the yellow solution with a white precipitate was filtered and the solvent was removed under reduced pressure. The residue was taken up in methylene chloride (ca. 500 mL) and filtered. The organic layer was extracted with water (1×300 mL), 5% acetic acid (3×120 ml), water (3×150 mL), dried (MgSO$_4$), filtered, and the solvent removed under reduced pressure to yield a cream solid (12.76 g, yield >99+%, purity by HPLC 63%). Chromatography of the solid on silica gel with ethyl acetate/hexane (5:2) gave a material yield of 62%, HPLC average purity 77%. Analytical sample (HPLC 95%). $[\alpha]_D^{20}$=−136.02° (c=0.98, THF). DSC m.p. 214°–219° C. $^1$H NMR (400 MHz, d6-DMSO) δ 9.38 (d, 2H, NH), 8.33 (1H, Ar-H), 7.85 (2H, Ar-H), 7.48 (m, 4H, Ar-H), 7.37 (m, 6H, Ar-H), 5.67 (d, 2H, HNCH), 3.66 (s, 6H, OMe), 2.30 (s, 3H, Me). $^{13}$C NMR (100 MHz, d$_6$-DMSO) δ 170.82 (COOMe), 169.07 (COMe), 165.1 (CONH), 150.08, 135.84, 134.93, 128.52, 128.25, 124.78, 124.24, (Ar-C), 57.05 (HNCH), 52.24 (OMe), 20.66 (Me). FTIR (KBr) v 3330, 3281, 3027, 2943, 1759 (sh), 1731 (S, C=O), 1639 (s, C=O) cm-1. MS(APCI(H$_2$O)+Q1) m/e 519.2 (M+1).

This end-capping monomer has the following structure:

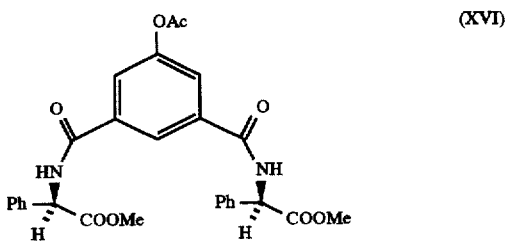

(XVI)

EXAMPLE 5

Preparation of Poly-(5-Hydroxyisophthalic Acid), (R)-2-Phenylglycine Methyl Ester Terminated Hyperbranched Polymer The end-cap (Example 4), [3-acetoxy-5-(methoxycarbonyl-phenyl-methylcarbamoyl)-benzoylamino]-phenyl-acetic acid methyl ester (6.29 g, 0.012 moles) was weighed into a 250 mL round bottom 1-neck flask. 5-Acetoxyisophthalic acid (3.03 g, 0.011 moles) was added to the flask. The flask was attached to an RE 111 Rotary Evaporator with a nitrogen blanket over the solids. The flask was rotated in an oil bath at a slow speed, approximately 1 rotation per second with heating. The mixture melted to a clear orange liquid in approximately 15 minutes at 206° C. After 30 minutes of heating, vacuum (~2.5 mmHg) was applied for 20 minutes and acetic acid distilled off. The dark red solid was cooled with rotation under vacuum to 70° C. and to ambient temperature under nitrogen. The solid was refluxed with tetrahydrofuran (170 mL) and water (17 mL) under nitrogen until dissolved (~10 minutes). The cooled solution was filtered and the solvent removed under reduced pressure. The residue was taken up in THF and filtered. The THF solution was added to water (700 mL) with stirring to precipitate the hyperbranched polymer. The hyperbranched polymer was filtered and dried to give an orange solid (2.62 g). $[\alpha]_D^{20}$=−2.979° C. (c=0.94, THF). GPC [THF using 4 Waters Ultrastyragel 7.8 mm×300 mm with 7 micron particle columns; standard polystyrene molecular weights 1800 to 500,000] Mw=1373 Daltons, polydispersity 1.6. TGA, ~257° C., 1H NMR (400 MHz, d$_6$-DMSO) δ 13.3 (vs), 9.41 (m), 8.42–7.85 (m), 7.47 (b), 7.34 Co), 5.68 (m), 3.66, 2.32 (m), THF peaks present. 13C NMR (50 MHz, d$_6$-DMSO) δ 171.31, 166.82–163.57 (m), 158.24 (b), 150.90, 136.36 (m), 130.59 (m), 119.79 (m), 56.96 (m), 52.23 (m), 20.74 (m), THF peaks present.

EXAMPLE 6

Preparation of Poly-(5-Hydroxyisophthalic Acid), (S)-Tryptophan Methyl Ester Terminated Hyperbranched Polymer The end-cap (Example 3) compound (10.2 g, 0.016 moles) was weighed into a 500 mL round bottom 1-necked flask. 5-Acetoxyisophthalic acid (7.18 g, 0.032 moles) was added to the flask. The flack was attached to a RE111 Rotary Evaporator with a nitrogen blanket over the solids. The flask was rotated in an oil bath at a slow speed, approximately 1 rotation per second with heating. The mixture melted to a yellow liquid at 215° C. After 15 minutes of heating, vacuum (~4mmHg) was applied for 30 minutes. The red solid was cooled with rotation under vacuum. The solid was refluxed with tetrahydrofuran (~100mL) under nitrogen for 1 hour. The cooled solution was filtered, reduced to a smaller volume of THF and 2-propanol was added to precipitate the hyperbranched polymer. The hyperbranched polymer was filtered and dried to give a yellow solid (2.11 g, 15%). $[\alpha]_D^{20}$=−39.4° (c=1.444, DMF). GPC Mw=5228 Daltons, polydispersity 1.4. TGA, ~262° C. 1H NMR (400 MHz, d$_6$-DMSO) δ 10.80, 9.06 (b), 8.8–6.9 (m), 4.73 Co), 3.62 (b), 3.26(vb) 2-propanol peaks present. 13 C NMR (50 MHz, d$_6$-DMSO) δ 172.49, 166.02 (m), 154.10, 163.13 (m), 150.94 (b), 136.26, 135.59, 128.35 (m), 127.19, 124.90, 123.75, 121.11, 118.55 (m), 118.12, 111.59, 109.93, 54.02, 51.97 (m), 26.57, 2-propanol peaks present.

The THF/2-propanol flitrate was evaporated down and a second precipitation of yellow hyperbranched polymer (2.35 g, 16%) was collected. $[\alpha]_D^{20}$=−42.805° C. (c=1.0980, DMF). GPC Mw=3695 Daltons, polydispersity 1.4.

The fitrate contained an orange-red solid (8.67 g, 60%). GPC Mw=1496 Daltons, polydispersity 1.4.

EXAMPLE 7

Preparation of Poly-(3,5-Dihydroxybenzoic Acid), (S)-(+)-Ibuprofen Terminated Hyperbranched Polymer (S)-(+)-Ibuprofen (10.01 g, 0.049 moles) was weighted into a 250 mL round bottom 1-necked flask. 3,5-Diacetoxybenzoic acid (12.06 g, 0.046 moles, Example 2) was added to the flask. The flask was attached to a RE111 Rotary Evaporator with a nitrogen blanket over the solids. The flask was tomted in an oil bath at a slow speed, approximately 1 rotation per second with heating. The mixture melted to a clear cream liquid in approximately 10 minutes at 162° C. After 40 minutes of heating at 200° C., vacuum (~1.75 mmHg) was applied for one hour and acetic acid distilled off. The cream solid was cooled under nitrogen to ambient temperature. The solid was refluxed 60 minutes with tetrahydrofuran (110 mL) under nitrogen. The cooled solution was filtered and half the solvent removed under reduced pressure. The THF solution was added to methanol (400 mL) with stirring to precipitate the hyperbranched polymer. The hyper- branched polymer was filtered and dried to give a cream solid(12.79 g, ~79%). $[\alpha]_D^{20}$=+6.298° (c=2.08, THF). GPC Mw=21805 Daltons, polydispersity 2.7. TGA, 390° C., 1H NMR (400 MHz, d$_6$-DMSO) δ 8.03 (b), 7.83–7.51 (m), 7.27 (b), 4.04 (b), 2.38 (b), 2.28 (b), 1.73, 1.49 (b), 0.833 (b), THF peaks presents. 13 C NMR (100 MHz, d$_6$-DMSO) δ 172.76, 168.73, 162.60, 151.01, 140.04, (m), 136.95, 130.61 (b), 127.13, 121.19 (m), 44.12, 29.42, 21.89, 20.63, 18.44 (m), THF peaks present.

EXAMPLE 8

Preparation of Poly-(3,5-Dihydroxybenzoic Acid), Benzoic Acid Terminaed Hyperbranched Polymer 3,5-Diacetoxybenzoic acid (63.50 g, 0.303 moles) was weighted into a 500 mL round bottom 1-necked flask. Benzoic acid (40.47 g, 0.328 moles) was added to the flask.

The flask was attached to a RE111 Rotary Evaporator with a nitrogen blanket over the solids. The flask was rotated in an oil bath at a slow speed, approximately 1 rotation per second with heating. The mixture melted to a yellow liquid in approximately 20 minutes at 190° C. After 47 minutes of heating at 200° C., vacuum (~1 mmHg) was applied for one hour and acetic acid distilled off. The cream solid was cooled under vacuum to ambient temperature. The solid was refluxed 60 minutes with tetrahydrofuran (400 mL) under nitrogen. THF (200 mL) was added to the cooled solution and the solution was filtered. Half the solvent was removed under reduced pressure. The THF solution was added to methanol (1000 mL) with stirring to precipitate the hyperbranched polymer. The hyperbranched polymer was filtered and dried to give a cream solid (50.29 g). GPC Mw=68015 Daltons, polydispersity 4.0. TGA ~345° C. 1H NMR (400 MHz, d$_6$-DMSO) δ 10.35 (b), 8.09 (b), 7.85 (b), 7.60 (b), 7.39 (b), 2.27 (b), methanol and water peaks present. 13 C NMR (100 MHz, d$_6$-DMSO) δ 168.81, 162.69, 135.00, 130.65–128.88 (m), 121.82–120.83 (m), 20.67, THF and methanol peaks present.

EXAMPLE 9

Preparation of Poly-(5-Hydroxyisophathalic Acid), (S)-Tryptophan Methyl Ester Terminated Hyperbranched Polymer The end-cap (Example 3) compound (6.45 g, 0.0098 moles, HPLC purity 66.3%) was weighed into a 500 mL round bottom 1-necked flask. 5-Acetoxyisophthalic acid (3.68 g, 0.0091 moles) was added to the flask. The flask was attached to a RE111 Rotary Evaporator with a nitrogen blanket over the solids. The flask was rotated in an oil bath at a slow speed, approximately 1 rotation per second with heating. The mixture melted to a yellow-orange liquid at 221° C. in 30 minutes. After 15 minutes of heating under nitrogen, vacuum (~1.5 mmHg) was applied for 30 minutes. The red solid was cooled with rotation under vacuum. The solid was refluxed with tetrahydrofuran (200 mL) under nitrogen for 10 minutes. The cooled solution was filtered, reduced to a smaller volume of THF and poured into water (700 mL) to precipitate the hyperbranched polymer. The hyperbranched polymer was filtered and dried to give a orange solid (6.62 g) [α]$_D^{20}$=–4.06° C. (c=3.82, THF). GPC Mw=2103 Daltons, polydispersity 1.7. TGA, 259° C. (onset). 1H NMR (400 MHz, d$_6$-DMSO) δ 10.80, 9.05 (b), 8.63–6.97 (m), 4.76 (b), 3.63 (b), 2.33, THF peaks present. 13 C NMR (100 MHz, d$_6$-DMSO) δ 172.42, 169.08 (m), 166.09–163.08 (m), 151(m), 136.10–118.40 (m), 111.44, 109.94, 53.85 (m), 51.85 (m), 26.61, THF peaks present.

EXAMPLE 10

Preparation of Poly-[2,2-Bis(Hydroxymethyl) Propionic Acid] Hyperbranched Polymer 2,2-Bis(hydroxymethyl)propionic acid (10.33 g, 0.077 moles) was weighed into a 500 mL round bottom 1-necked flask. The flask was attached to a RE111 Rotary Evaporator with a nitrogen/argon blanket over the solids. The flask was rotated in an oil bath at a slow speed, approximately 1 rotation per second with heating. The mixture melted to a clear liquid in approximately 25 minutes at 200° C. After 13 minutes of heating at 200° C., vacuum (~3.25 mmHg) was applied for 1.3 hours and water distilled off. The clear pale yellow solid was cooled under vacuum to ambient temperature. Starting material was removed from the neck of the flask and THF (~100 mL) was added to the clear glassy solid. After standing over night the white starting material was removed and the THF removed under reduced pressure to give a clear semi-solid (5.6 g). GPC Mw=1768 Daltons, polydispersity 1.6. TGA ~270° C. 1H NMR (400 MHz, d$_6$-DMSO)δ 11.65, 4.9 (b), 4.59(b), 4.06, 3.47(m), 1.06(m). 13C NMR (100 MHz, d$_6$-DMSO)δ 174.3(m), 173.1(m), 63.88(bm), 50.25–45.64(m), 16.87 (m).

EXAMPLE 11

In order to demonstrate the chelating utility of this highly branched polymer, 10 g of the polymer is produced according to the process described in Example 5. A 1% solution of copper sulfate (1000 ppm CuSO$_4$ is combined with 100 ml of water to produce a light blue solution containing copper ions. The 10 g of polymer product is added, with stirring, to this solution. The resultant material is filtered to remove the copolymer-copper complex and the flitrate, which is clear and colorless is tested for copper sulfate content. The filtrate analyzes less than 10 ppm CuSO$_4$.

In another facet of the present invention, it has also been found that the "core monomers" disclosed in U.S. Pat. No. 5,362,843 can also be used in formulating new hyperbranched polymers. In this aspect, the branching monomer, end-capping monomer and core monomer are mixed together at a sufficient temperature and for a sufficient period of time to produce the desired polymer.

The core monomer used in this facet of the present invention includes the following seven categories of compounds (i.e. A–H):

A. dihydric phenol having the following formula:

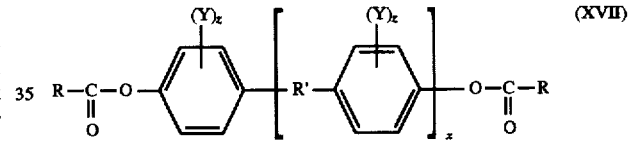

(XVII)

wherein R is independently selected from hydrogen, an alkyl radical having from 1 to about 6 carbon atoms, preferably methyl, cycloalkyl having from 4 to about 7 carbon atoms, or aryl, Y is independently selected from alkyl groups of 1 to 4 carbon atoms, chlorine or bromine, z independently has a value of from 0 to 4, inclusive, and R' is independently selected from a divalent saturated aliphatic hydrocarbon radical, particularly alkylene or alkylidene radicals having from 1 to 8 carbon atoms or halogermnted derivatives thereof, especially C(CH$_3$)$_2$, C(CX$_3$)$_2$; wherein X is a halogen, preferably fluorine, cycloalkylene or cycloallcylidene radicals having up to and including 9 carbon atoms, halogenated derivatives thereof, O, S, SO, SO$_2$, CO; and x is 0 or 1.

The dihydric phenols that may be used in this invention include but are not limited to the following:
2,2-bis-(4-hydroxyphenyl)propane,
2,2-bis-(4-hydroxyphenyl)hexafluoropropane,
bis-(2-hydroxyphenyl)methane,
bis-(4-hydroxyphenyl)methane,
bis-(4-hydroxy-2,6-dimethyl-3 -methoxyphenyl) methane,
1,1-bis-(4-hydroxyphenyl)ethane,
1,2-bis-(4-hydroxyphenyl)ethane,
1,1-bis-(4-hydroxy-2-chlorophenyl)ethane,
1,1-bis-(3-methyl-4-hydroxyphenyl)ethane,
1,3-bis-(3 -methyl-4-hydroxyphenyl)propane,
2,2-bis-(3-phenyl-4-hydroxyphenyl)propane,
2,2-bis-(3-isopropyl-4-hydroxyphenyl)propane,
2,2-bis-(2-isopropyl-4-hydroxyphenyl)propane,
2,2-bis-4-hydroxyphenyl)pentane, 3,3-bis-(4-hydroxyphenyl)pentane, 2,2-bis-(4-hydroxyphenyl)heptane, 1,2-bis-(4-hydroxyphenyl)- 1,2-bis-(phenyl)-propane, 4,4'-(dihydroxyphenyl)ether, 4,4'- (dihydroxyphenyl)sulfide, 4,4'- (dihydroxyphenyl)sulfone, 4,4'-(dihydroxyphenyl)sulfoxide, 4,4'-(dihydroxybenzophenone), hydroquinone, and naphthalene diols.

These dihydric phenols may be used individually or in any combination. It is also possible to add up to 50 wt. % based on the total diol content of aliphatic diols, such as neopentyl glycol. One common dihydric phenol is 2,2-bis (4-hydroxyphenyl)propane (bisphenol-A).

B.

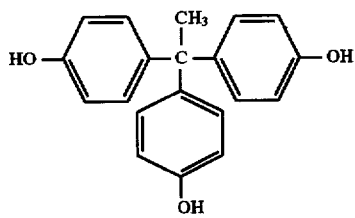 (XVIII)

C.

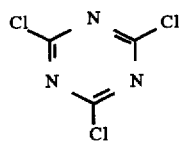 (XIX)

Cl can also be replaced with other halogens such as Br and F.

D.

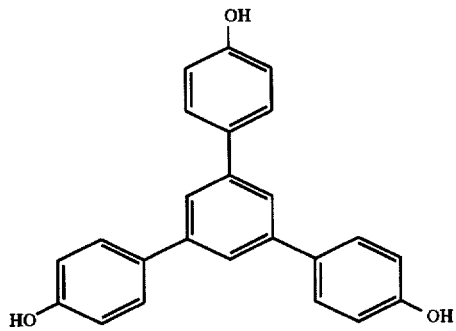 (XX)

E.

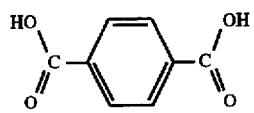 (XXI)

F.

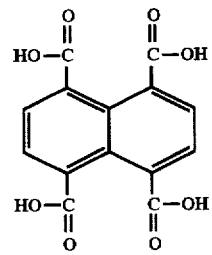 (XXII)

G.

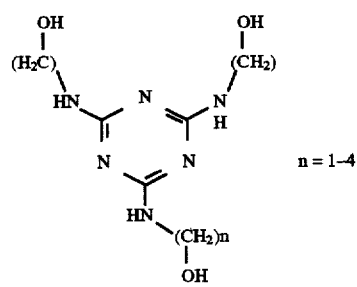 (XXIII)

n = 1–4

H.

(XXIV)

where R is H, alkyl ($C_1$–$C_{20}$) and aromatic.

These hyperbranched polymers are prepared by rest mixing and heating the branched monomer and core monomer together followed by the addition of end-capping monomer. In this 3 component system, the core monomer is used in the range of 0.001% by weight to about 20.0% by weight based on the weight of the 3 monomers combined.

The polymerization takes place under the same conditions as set forth herein as it pertains to the 2 component (i.e. branching monomer and end-capping monomer) system.

EXAMPLE 12

Polymerization of 3,5-Diacetoxybenzoic Acid with 1,1,1-Tris(4-Acetoxyphenyl)Ethane (THPE-Triacetate) as Monomer Core in Dowtherm A 3,5-Diacetoxybenzoic acid (9.67 g, 41 mmol), 1,1,1-tris (4-acetoxyphenyl)ethane (1 g, 2 mmol), Dowtherm A (100 g) and KOAc (0.01 g) were placed into a 3-neck round bottom flask fitted with a thermowell, mechanical stirrer, and distillation head. The Dowtherm A was used to help reduce the melt viscosity. The polymerization was conducted at 260° C. for 2 hours. A brown solid was isolated by precipitating the dendrimer into MeOH. The brown solid was filtered and dried under vacuum. 13C NMR (CDCl$_3$) δ 168.93, 163.55, 162.67, 157.38, 151.22, 148.95, 146.48, 146.09, 131.66, 130.94, 130.76, 129.74, 128.77, 123.23, 121.30, 120.93, 116.88, 115.26, 51.59, 30.5, 20.84. The peaks at 166 and 115 in the 13C NMR indicate partial hydrolysis of the acetate end-groups.

EXAMPLE 13

Two grams of the product (Example 12) is polymerized with 4 grams of end-capping monomer (Example 3) under the conditions of Example 12. The end product is light brown and NMR indicates the attachment of the end-capping monomer.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing an aryl compound having the formula

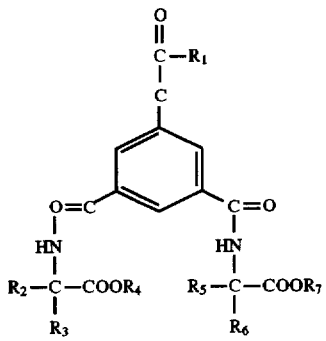

wherein $R_1$–$R_7$ are each independently selected from the group consisting of
   (a) hydrogen
   (b) alkyl $C_1$–$C_{20}$
   (c) alkoxy alkyl having 1 to 8 carbon atoms in both alkoxy group and alkyl group
   (d) phenyl
   (e) naphthyl, and
   (f) indole, which comprises the steps of (a) reacting a phenyl dicarboxylic acid with a carboxylic acid activating functionally for a sufficient period of time and at a temperature of from about –20° C. to about 120° C. to form an activated intermediate, and (b) reacting said activated intermediate with a suitable nucleophile for a sufficient period of time and at a temperature of from about –20° C. to about 120° C. to form said aryl compound.

2. The process as set forth in claim 1 wherein the aryl compound has the formula

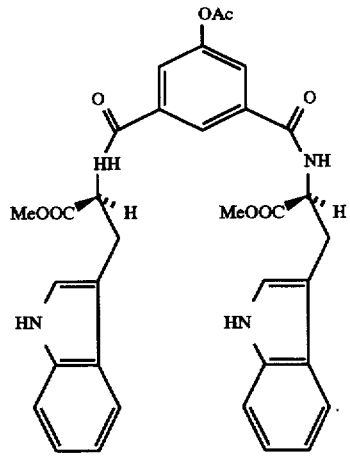

3. The process as set forth in claim 1 wherein the aryl compound has the formula

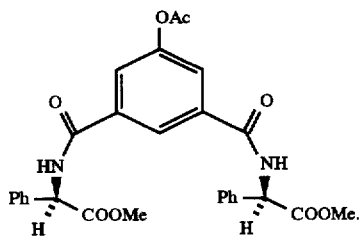

* * * * *